United States Patent [19]

Boden et al.

[11] 4,376,058
[45] Mar. 8, 1983

[54] MIXTURE OF ALIPHATIC $C_{10}$ BRANCHED OLEFIN EPOXIDES AND USE THEREOF IN AUGMENTING OR ENHANCING THE AROMA OF PERFUMES AND/OR ARTICLES

[75] Inventors: Richard M. Boden, Monmouth Beach; Lambert Dekker, Wyckoff; Frederick L. Schmitt, Holmdel, all of N.J.; Augustinus G. Van Loveren, Rye, N.Y.

[73] Assignee: International Flavors & Fragrances Inc., New York, N.Y.

[21] Appl. No.: 350,094

[22] Filed: Feb. 18, 1982

Related U.S. Application Data

[60] Division of Ser. No. 195,630, Oct. 9, 1980, Pat. No. 4,335,009, which is a continuation-in-part of Ser. No. 160,788, Jun. 19, 1980, Pat. No. 4,287,084.

[51] Int. Cl.$^3$ .............................................. C11D 3/50
[52] U.S. Cl. ........................... 252/174.11; 252/522 R; 549/512
[58] Field of Search ...................... 252/174.11, 522 R; 549/512

[56] References Cited

U.S. PATENT DOCUMENTS 4,304,689 12/1981 Boden et al. .................... 252/522 R Primary Examiner—John E. Kittle
Assistant Examiner—Robert A. Wax
Attorney, Agent, or Firm—Arthur L. Liberman

[57] ABSTRACT

Described are methods for augmenting or enhancing the aroma of perfumes and perfumed articles by adding thereto perfume aroma augmenting or enhancing quantities of novel $C_{10}$-branched olefin epoxide mixtures produced by dimerizing isoamylene, (2-methyl-2-butene) and then epoxidizing the resulting product; as well as perfume compositions, colognes and perfumed articles including solid or liquid anionic, cationic, nonionic or zwitterionic detergents, fabric softener compositions, hair preparations and deodorant compositions as well as bleaching compositions containing same.

2 Claims, 13 Drawing Figures

GLC PROFILE FOR EXAMPLE I.

GLC PROFILE FOR EXAMPLE I.

GLC PROFILE FOR EXAMPLE I.

GLC PROFILE FOR EXAMPLE I.

GLC PROFILE FOR EXAMPLE I.

GLC PROFILE FOR EXAMPLE I.

GLC PROFILE FOR EXAMPLE I.
DISTILLATION PRODUCT.

GLC PROFILE FOR EXAMPLE I.
CRUDE PRODUCT.

NMR SPECTRUM FOR PEAK I OF EXAMPLE I, OF GLC OF FIG.1E

IR SPECTRUM FOR EXAMPLE I, PEAK I, OF GLC OF FIG.1E.

FIG. 3A
NMR SPECTRUM FOR EXAMPLE I, PEAK 2, OF GLC OF FIG. 1E
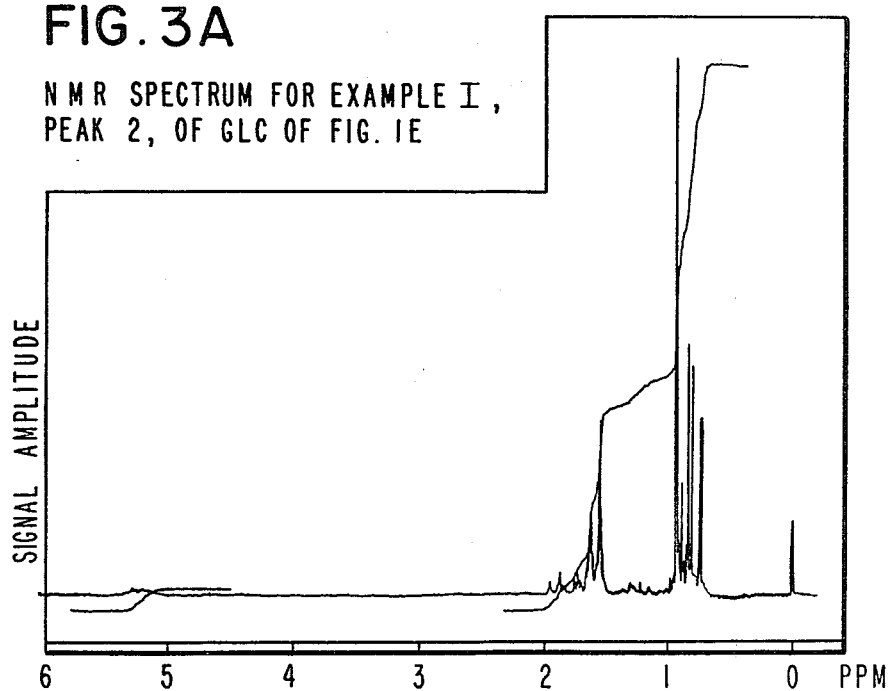
IR SPECTRUM FOR EXAMPLE I, PEAK 2 OF GLC OF FIG. 1E
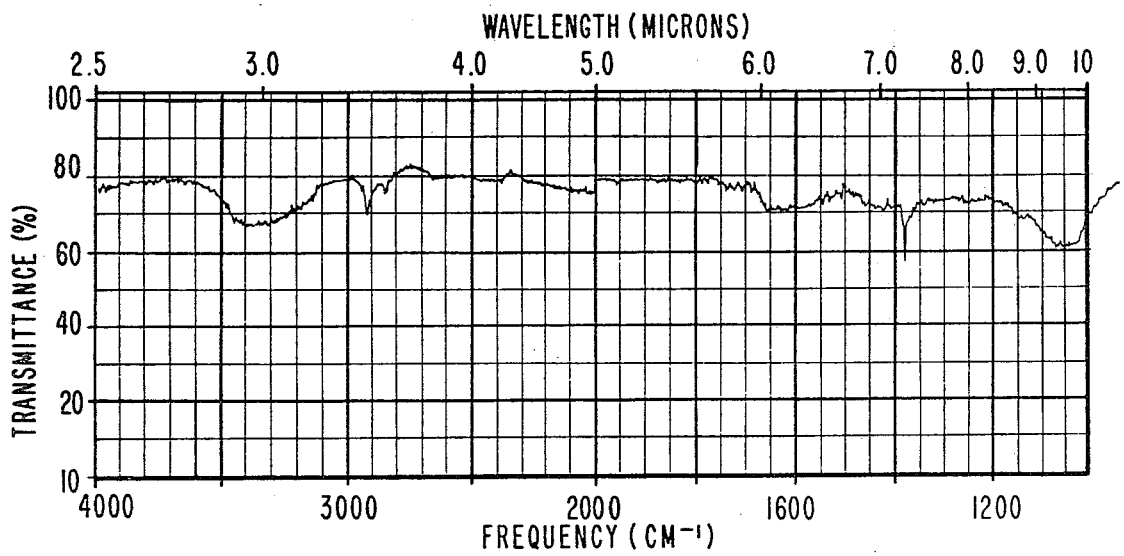
FIG. 3B

NMR SPECTRUM FOR PEAK 2 OF EXAMPLE I, OF GLC OF FIG. 1B.

GLC PROFILE FOR EXAMPLE II.

NMR SPECTRUM FOR EXAMPLE II.

IR SPECTRUM FOR EXAMPLE II.

MIXTURE OF ALIPHATIC C₁₀ BRANCHED OLEFIN EPOXIDES AND USE THEREOF IN AUGMENTING OR ENHANCING THE AROMA OF PERFUMES AND/OR ARTICLES

This is a division of application Ser. No. 195,630, filed Oct. 9, 1980, now U.S. Pat. No. 4,335,009, which in turn, is a continuation-in-part of application for U.S. Letters Patent Ser. No. 160,788 filed on June 19, 1980, now U.S. Pat. No. 4,287,084 issued on Sept. 1, 1981.

BACKGROUND OF THE INVENTION

The instant invention provides mixtures of $C_{10}$ branched chain olefin epoxides which are used to augment or enhance the aroma of perfume compositions, colognes and perfumed articles.

Chemical compounds which can provide a woody, eucalyptol and minty aroma are desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree, or they contribute undesirable or unwanted odor to the compositions.

Aliphatic hydrocarbons are well known in the art of perfumery, e.g. myrcene, 2-methyl-6-methylene-2,7-octadiene, a constituent of lemon grass oil. Also found in lemon oil as well as in Bergamot oil, according to Gildemeister and Hoffmann, (Die Atherischen Ole, 3rd edition, Volume 1, page 301) is octylene, a long chain olefin containing eight carbon atoms.

Arctander, "Perfume and Flavor Chemicals, (Aroma Chemicals)", 1969, Vol. I, at monograph 974, discloses the use of "di-isoprene" in perfumery. Arctander states that di-isoprene is a mixture of 2,6-dimethyl-2,6-octadiene; 2,7-dimethyl-2,6-octadiene; and 3,6-dimethyl-2,6-octadiene. Arctander states that this material has a sweet, diffusive, somewhat "gassy" odor and, overall, is of very "little interest to the perfumer." At monograph 1074, Arctander discloses "dipentene" having a use in perfumery and indicates that this "dipentene" is 1-methyl-4-iso-propenyl-1-cyclohexene and indicates that it is useful in perfumery as a "lift" in citrusy fragrances and in the reconstruction of many essential oils such as Bergamot, Lime and Lemon.

U.S. Pat. No. 3,896,180 issued on July 22, 1975 discloses the use in perfumery of the cyclic diene epoxide having the structure:

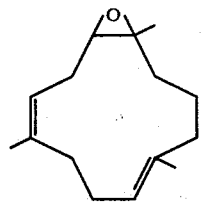

particularly for its woody, amber odor.

Other mono-epoxidized products of tri-methylcyclododecatriene are disclosed in U.S. Pat. No. 3,723,478 issued on Mar. 27, 1973. The uses in perfumery of such materials are also disclosed in said U.S. Pat. No. 3,723,478.

U.S. Pat. No. 3,333,010 issued on July 25, 1957 discloses epoxycyclododecadiene having the structure:

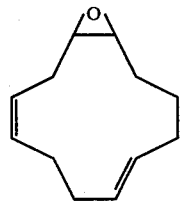

Nothing in the prior art however, discloses the compounds defined according to the generic structure:

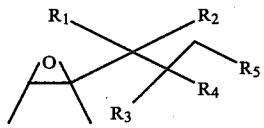

which would be produced from branched chain olefins having the generic structure:

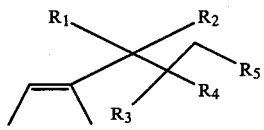

wherein $R_1$, $R_2$, $R_3$, $R_4$ and $R_5$ are the same or different and each represents hydrogen or methyl with the proviso that (i) the sum total of carbon atoms in $R_1$, $R_2$, $R_3$, $R_4$ and $R_5$ is three, and (ii) $R_1$ and $R_2$ represents hydrogen when $R_5$ represents methyl, and (iii) when either $R_1$ or $R_2$ is methyl, $R_5$ is hydrogen, the epoxide compounds being represented by the structures:

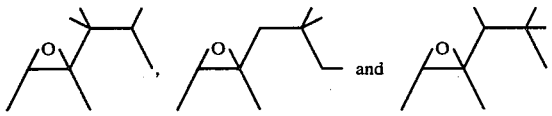

"Di-isoamylene" is indicated to be synthesized in the following references:

i—Murphy & Lane, Inc. Eng. Chem., Prod. Res. Dev., Vol. 14, No. 3, 1975 p. 167 (Title: Oligomerization of 2-Methyl-2-Butene in Sulfuric Acid and Sulfuric-Phosphoric Acid Mixtures).

ii—Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes)

iii—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II)

iv—U.S. Pat. No. 3,627,700, issued on Dec. 14, 1971, (Zuech)

v—U.S. Pat. No. 3,538,181, issued on Nov. 3, 1970, (Banks)

vi—U.S. Pat. No. 3,461,184, issued on Aug. 12, 1969 (Hay, et al)

vii—Gurwitsch, Chemische Berichte, 1912, Vol. 2, p. 796 (Production of Di-isoamylene From Isoamylene Using Mercury Acetate Catalyst)

United Kingdom Pat. No. 796,130 published on June 4, 1958 discloses the synthesis of polyalkylindanes by means of, interalia, reacting alpha-methylstyrene with trimethylethene (2-methyl-butene-2) in the presence of an acid catalyst such as, sulfuric acid or boron trifluoride methyletherate It is further indicated that such compounds are useful intermediates in the production of perfumery compounds. Apparently however, the more volatile di-isoamylenes produced as side-products in the reaction of 2-methyl-butene-2 with alpha-methylstyrene are discarded.

BRIEF DESCRIPTION OF THE DRAWINGS

FIG. 3A represents the NMR spectrum for Peak 2 of the GLC profile of FIG. 1E.

FIG. 3B represents the infra-red spectrum for Peak 2 of the GLC profile of FIG. 1E.

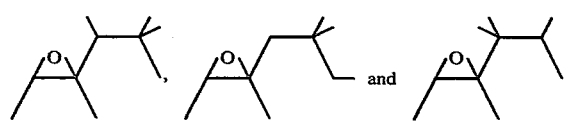

Figure 6:
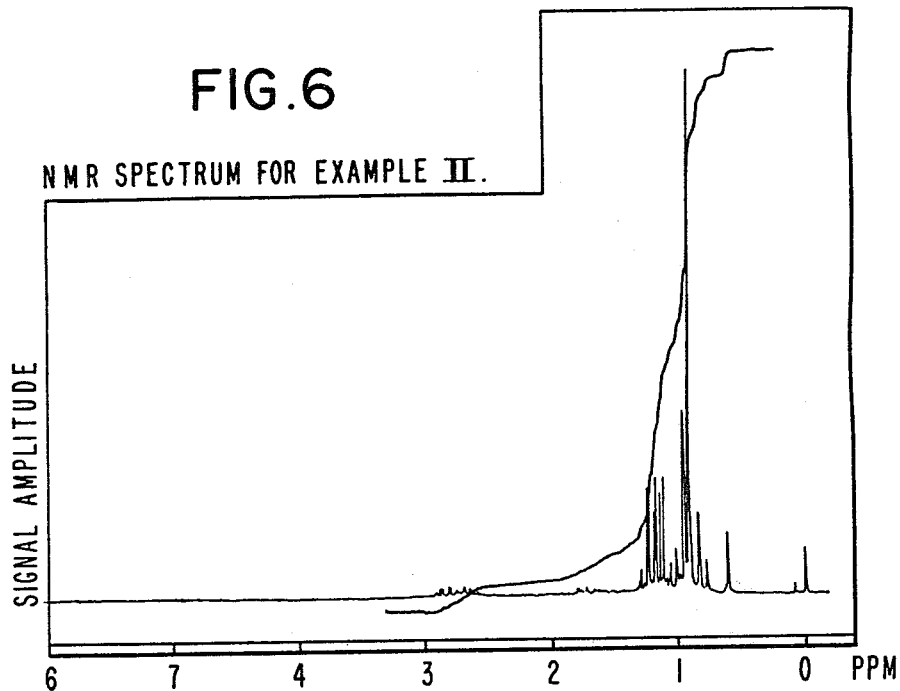

FIG. 6 is the NMR spectrum for the reaction product of Example II containing the compounds having structures:

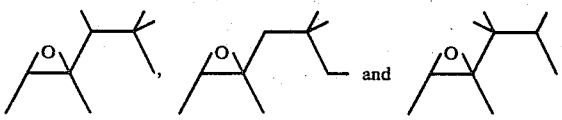

Figure 7:
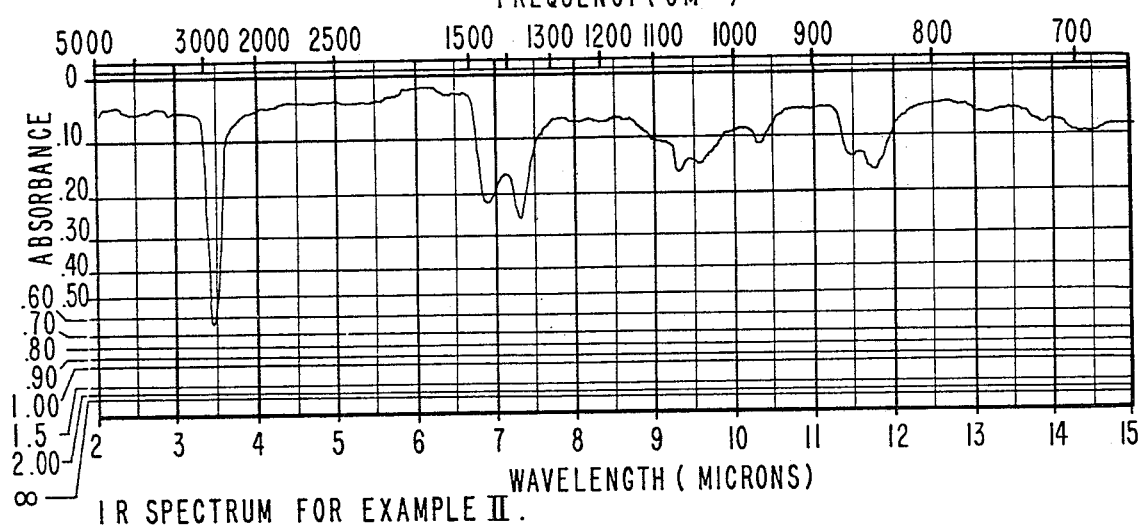

FIG. 7 is the infra-red spectrum for the reaction product of Example II containing the compounds having the structures:

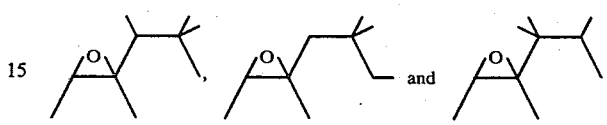

THE INVENTION

It has now been determined that epoxides of dimers of isoamylene produced according to the reaction sequence:

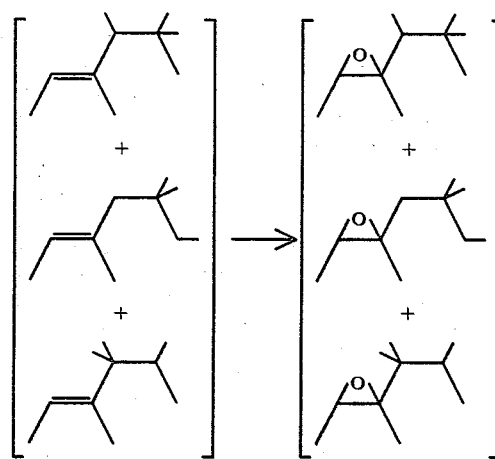

are capable of imparting or augmenting or enhancing a variety of fragrances to consumable materials.

Briefly our invention contemplates augmenting or enhancing fragrances of such consumable materials as perfumes, perfumed articles (e.g., solid or liquid anionic, cationic, nonionic, or zwitterionic detergents, cosmetic powders, fabric softener compositions and dryer-added fabric softener articles) and colognes by adding thereto, a small, but effective amount of at least one of the compounds defined according to one of the structures:

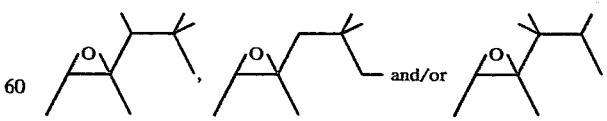

The di-isoamylene epoxide compounds of our invention augment or enhance woody, eucalyptol and minty aroma characteristics of perfumes, perfumed articles and colognes, thereby causing one or more of said di-isoamylene eposide compounds to be useful particularly in "eucalyptus" type fragrances. Furthermore, the diisoamylene epoxide compounds of our invention have unexpected and unobvious stability, particularly in the presence of strong oxidizing agents such as hypochlorite bleach solutions. Thus, the diisoamylene epoxide compounds of our invention can be used particularly to augment or enhance the aroma of perfumed bleach compositions, particularly perfumed hypochlorite bleached compositions.

The di-isoamylene epoxide derivatives of our invention, having the structures:

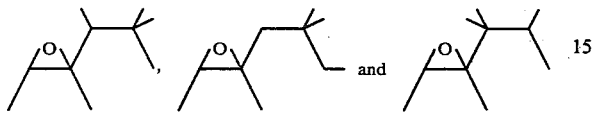

were defined according to the generic structure:

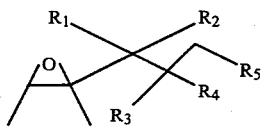

wherein $R_1$, $R_2$, $R_3$, $R_4$ and $R_5$ are the same or different and each represents hydrogen or methyl with the proviso that (i) the sum total of carbon atoms in $R_1$, $R_2$, $R_3$, $R_4$ and $R_5$ is three, and (ii) $R_1$ and $R_2$ represents hydrogen when $R_5$ represents methyl, and (iii) when either $R_1$ or $R_2$ is methyl, $R_5$ is hydrogen, may be prepared by first reacting 2-methyl-2-butene in the presence of an acidic catalyst which may a Lewis acid such as, zinc chloride, aluminum chloride, aluminum bromide, diethyl aluminum chloride, diethyl aluminum bromide, ethyl di-aluminum chloride and ethyl di-aluminum bromide, boron trifluoride, boron trifluoride ethyrate, or any of the other catalysts enumerated in the following references:

i—Murphy & Lane, Ind. Eng. Chem., Prod. Res. Dev., Vol. 14, No. 3, 1975 p. 167 (Title: Oligomerization of 2-Methyl-2-Butene in Sulfuric and Sulfuric-Phosphoric Acid Mixtures).

ii—Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes)

iii—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II)

iv—U.S. Pat. No. 3,627,700, issued on Dec. 14, 1971, (Zuech)

v—U.S. Pat. No. 3,538,181, issued on Nov. 3, 1970, (Banks)

vi—U.S. Pat. No. 3,461,184, issued on Aug. 12, 1969 (Hay, et al)

vii—Gurwitsch, Chemische Berichte, 1912, Vol. 2, p. 796 (Production of Di-isoamylene From Isoamylene Using Mercury Acetate Catalyst)

Thereby forming the compounds having the structures:

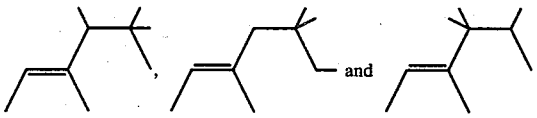

which are defined by the generic structure:

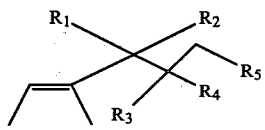

wherein $R_1$, $R_2$, $R_3$, $R_4$ and $R_5$ are the same or different and each represents hydrogen or methyl with the proviso that (i) the sum total of carbon atoms in $R_1$, $R_2$, $R_3$, $R_4$ and $R_5$ is three, and (ii) $R_1$ and $R_2$ represent hydrogen when $R_5$ represents methyl, and (iii) when either $R_1$ or $R_2$ is methyl, $R_5$ is hydrogen.

The one or more of the compounds having the structures:

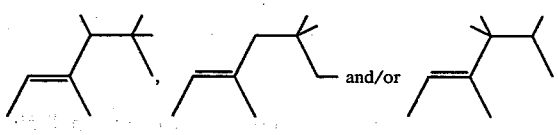

is then epoxidized using a suitable epoxidizing agent according to the conditons as set forth in either of U.S. Pat. No. 3,896,180 issued on July 22, 1975 or U.S. Pat. No. 3,723,478 issued on Mar. 27, 1973.

In so far as the first reaction is concerned, forming the compounds having the structures:

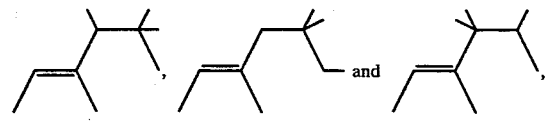

depending upon the conditions of reaction, including temperature, pressure, mole ratio of 2-methyl-2-butene:-catalyst, concentration of 2-methyl-2-butene in solvent, concentration of catalyst in solvent and time of reaction, the ratio and nature of the isomers having the structures:

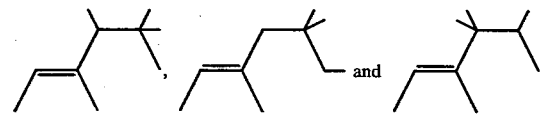

will vary in an as yet undetermined fashion. In any event, this invention contemplates the use as precursors of all isomers of di-isoamylene defined according to the structures:

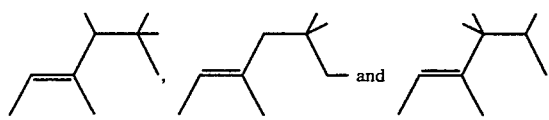

or the generic structure:

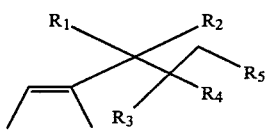

wherein $R_1$, $R_2$, $R_3$, $R_4$ and $R_5$ are the same or different and each represents hydrogen or methyl with the proviso that (i) the sum total of carbon atoms in $R_1$, $R_2$, $R_3$, $R_4$ and $R_5$ is three, and (ii) $R_1$ and $R_2$ represent hydrogen and $R_5$ represents methyl, and (iii) when either $R_1$ or $R_2$ is methyl, $R_5$ is hydrogen.

Insofar as the second reaction to form the compounds having the structures:

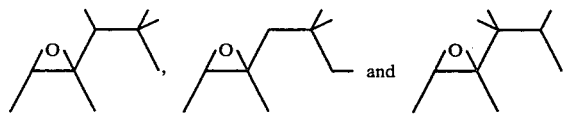

depending upon the conditions of reaction, including temperature pressure, mole ratio of compounds having the structures:

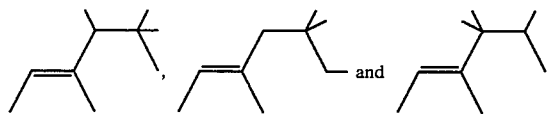

to catalyst, concentration of compounds having the structures:

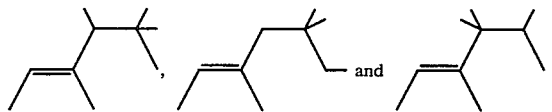

in solvent, concentration of catalyst, e.g. peracetic acid, perbenzoic acid or perphthalic acid in solvent and time of reaction, the ratio and nature of isomers having the structures:

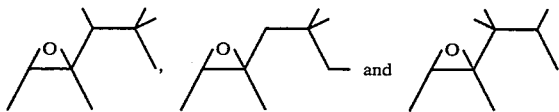

will vary in an as yet undetermined fashion. In any event, this invention contemplates the use of all isomers of the di-isoamylene epoxide defined according to the generic structure:

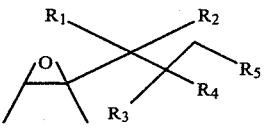

wherein $R_1$, $R_2$, $R_3$, $R_4$ and $R_5$ are the same or different and each represents hydrogen or methyl with the proviso that (i) the sum total of carbon atoms in $R_1$, $R_2$, $R_3$, $R_4$ and $R_5$ is three, and (ii) $R_1$ and $R_2$ represent hydrogen and $R_5$ represents methyl, and (iii) when either $R_1$ or $R_2$ is methyl, $R_5$ is hydrogen, taken alone or in admixture in all proportions when used in augmenting or enhancing the aroma of perfume compositions, perfumed articles and colognes.

As olfactory agents, the di-isoamylene epoxide derivatives, taken alone or in admixture, of our invention can be formulated into, or used as components of a "perfume composition" or can be used as components of a "perfumed article", or the perfume composition may be added to perfumed articles.

The term "perfume composition" is used herein to mean a mixture of organic compounds including, for example, alcohols, aldehydes, ketones, nitriles, ethers, lactones, epoxides, other than the di-isoamylene epoxide derivatives of the instant invention, natural essential oils, synthetic essential oils and hydrocarbons which are admixed so that the combined odors of the individual components produce a pleasant or desired fragrance. Such perfume compositions usually contain (a) the main note or the "bouquet" or formulation stone of the composition; (b) modifiers which round off and accompany the main note; (c) fixatives which include odorous substances which lend a particular note to the perfume throughout all stages of evaporation, and substances which retard evaporation; and (d) top notes which are usually low boiling, fresh-smelling materials.

In perfume compositions, the individual component will contribute its particular olfactory characteristics, but the overall effect of the perfume composition will be the sum of the effects of each of the ingredients and in certain instances, a synergistic effect as a result of the addition of certain ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the di-isoamylene epoxide derivative(s) of this invention which will be effective in perfume compositions depends on many factors, including the other ingredients, their amounts and the effects which are desired. It has been found that perfume compositions containing as little as 0.05% of the di-isoamylene epoxide derivative(s) of this invention, or even less, can be used to impart an interesting, woody, eucalyptol-like and minty aroma to soaps, liquid or solid anionic, cationic, nonionic or zwitterionic, detergents, cosmetics, cosmetic powders, liquid and solid fabric softeners, dryer-added fabric softener articles (e.g. BOUNCE ® a registered trademark of the Procter & Gamble Company of Cinncinati, Ohio), optical brightener compositions, hypochlorite bleach compositions and other products. The amount employed can range up to 70% or even higher, and will depend on considerations of cost, nature of the end product and the effect desired on the finished product and particular fragrance sought. Thus, for example, when fragrancing liquid bleach compositions containing alkali metal hypochlorite, such as, for example, sodium hypochlorite, for example CLO-ROX ®, (registered trademark of CHLOROX, Inc.). The amount employed can be as high as 100% of the fragrance involved in the liquid bleach. Indeed, a distinctive aspect of our invention is the use of one or more of the di-isoamylene epoxide derivative(s) in a stable liquid bleach composition.

The di-isoamylene epoxide derivative(s) of this invention, taken alone or in admixture, can be used alone, or in a perfume composition as an olfactory component in detergents, soaps, space odorants and deodorants; perfumes; colognes, toilet waters; bath salts; hair preparations, such as lacquers, brillantines, pomades and shampoos; cosmetic preparations, such as creams, deodorants, hand lotions, sunscreens; powders, such as talcs, dusting powders, face powders and the like; liquid bleaches, such as sodium hypochlorite—containing bleaches; floor waxes; automobile aromas and automobile polish compositions. When used as an olfactory component of a perfumed article, as little as 0.01% of one or more of the di-isoamylene epoxide derivative(s) will suffice to impart an interesting, eucalyptol-like, minty and woody aroma. Generally, no more than 015% is required to impart such aromas, however, in view of the rather low cost of the di-isoamylene epoxide derivative(s) of our invention, up to 100% of the perfume composition, can be one or more of the di-isoamylene epoxide derivative(s).

In addition, the perfume composition can contain a vehicle or carrier for the di-isoamylene epoxide derivative(s), alone, or with other ingredients. The vehicle can be a liquid such as a non-toxic alcohol such as ethanol, a glycol such as propylene glycol, or the like. The carrier can be an absorbent solid, such as a gum or components for encapsulating the composition such as gelatin which can be used to form a capsule wall surrounding the perfume oil, as by means of coacervation.

It will thus be apparent that the di-isoamylene epoxide derivative(s) of our invention can be utilized to alter, modify, augment or enhance sensory properties, particularly organoleptic properties such as fragrances of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

PREPARATION OF DI-ISOAMYLENE DERIVATIVES

Reaction:

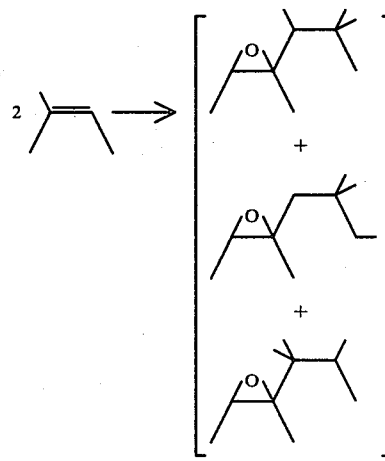

Di-isoamylene is prepared according to one of the procedures set forth in the following references:

i—Murphy & Lane, Ind. Eng. Chem., Prod. Res. Dev., Vol. 14, No. 3, 1975 p. 167 (Title: Oligomerization of 2-Methyl-2-Butene in Sulfuric and Sulfuric-Phosphoric Acid Mixtures).

ii—Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes)

iii—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II)

iv—U.S. Pat. No. 3,627,700, issued on Dec. 14, 1971, (Zuech)

v—U.S. Pat. No. 3,538,181, issued on Nov. 3, 1970, (Banks)

vi—U.S. Pat. No. 3,461,184, issued on Aug. 12, 1969 (Hay, et al)

vii—Gurwitsch, Chemische Berichte, 1912, Vol. 2, p. 796 (Production of Di-isoamylene From Isoamylene Using Mercury Acetate Catalyst)

As an illustration, and not by way of limitation, the following Example sets forth the preparation of di-isoamylenes useful in producing the fragrances of our invention:

Over a period of ten hours, 2-methyl-2-butene is pumped through a 5'×⅜ (0.625 inch) tube packed with 15.0 g of polystyrene sulfonic acid catalyst, at a temperature of 100° C. and at a pressure of 400 psig.

The resulting material was distilled in a fractionation column in order to separate the di-isoamylene from the higher molecular weight polymers, which are formed during the reaction as by-products.

Figure 1A:
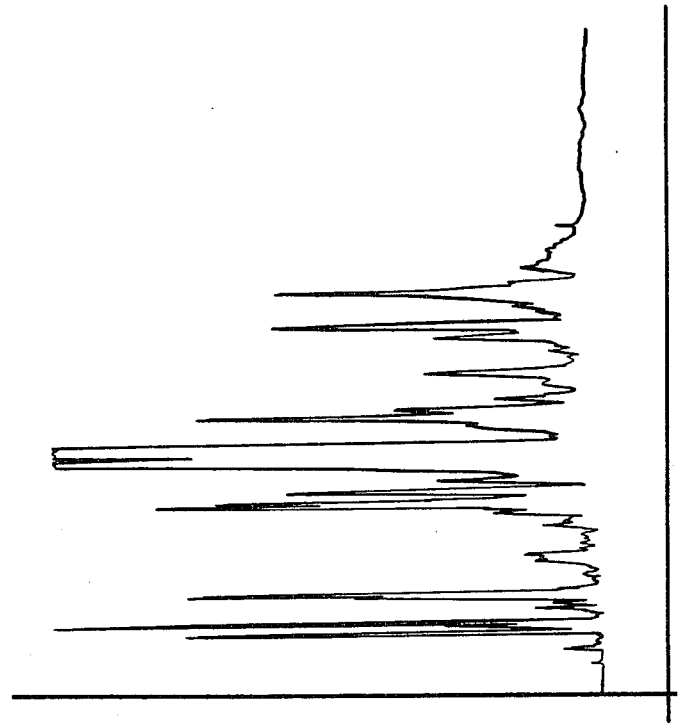
FIG. 1A represents the GLC profile for the reaction product of Example I using a 70% sulfuric acid catalyst at 35° C.

FIG. 1A represents the GLC profile for the reaction product of Example I using a 70% sulfuric acid catalyst at 35° C.

Figure 1B:
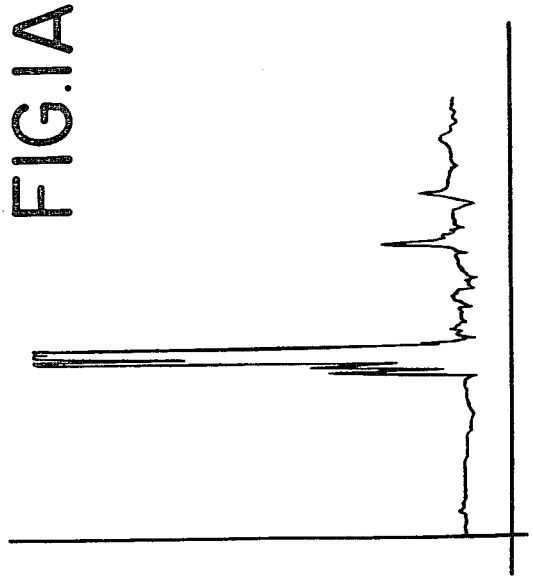
FIG. 1B represents the GLC profile for the reaction product of Example I using an Amberlyst ® 15 acidic ion exchange resin catalyst at a temperature of 150° C.

FIG. 1B represents the GLC profile for the reaction product of Example I using an Aberlyst ® 15 acedic ion exchange resin catalyst at a temperature of 150° C.

Figure 1C:
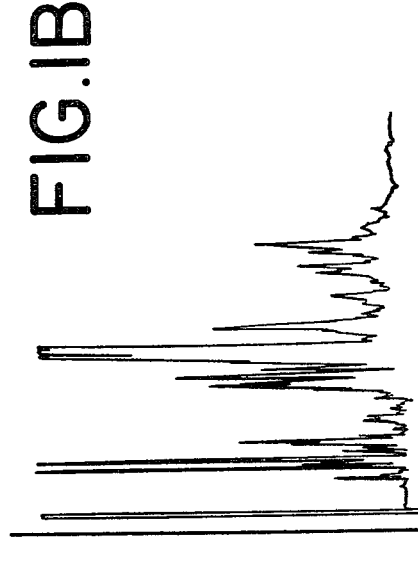
FIG. 1C represents the GLC profile for the reaction product of Example I, using an Amberlyst ® 15 catalyst at 100° C.

FIG. 1C represents the GLC profile for the reaction product of Example I, using an Amberlyst ® 15 catalyst at 100° C.

Figure 1E:
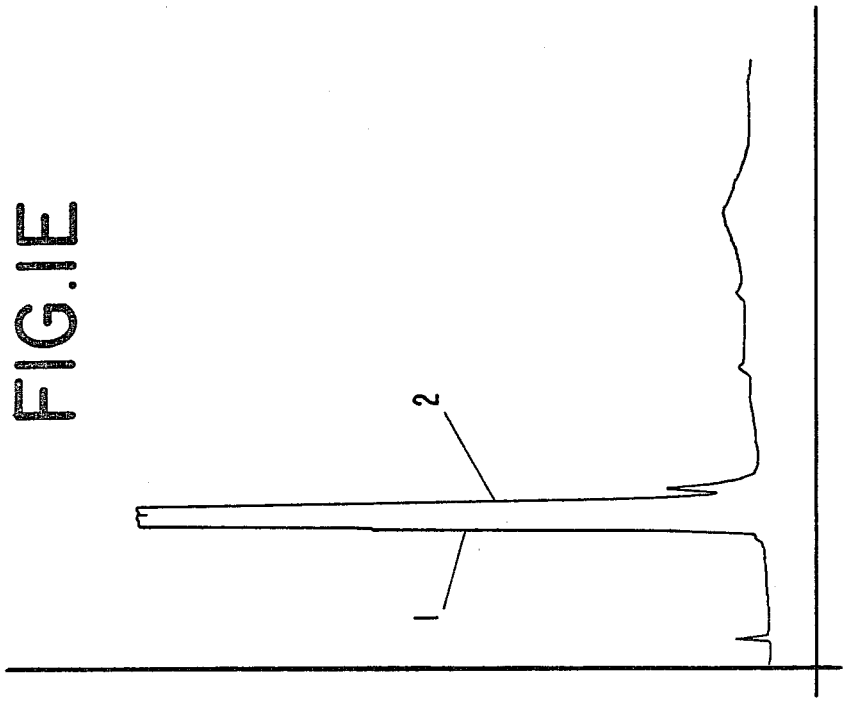
FIG. 1E represents the GLC profile for the reaction product of Example I, using a sulfuric acid catalyst, at 35° C. and an alpha-methylstyrene diluent according to the conditions of United Kingdom Pat. No. 796,130 (distilled reaction product).
Figure 1D:
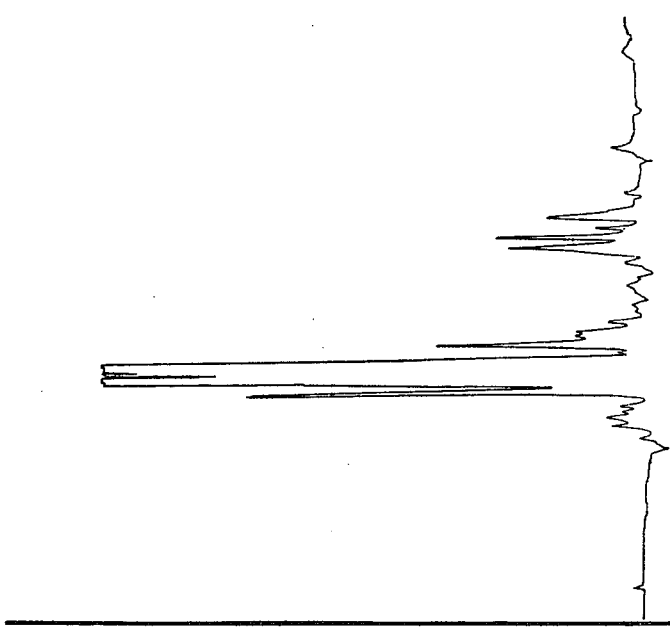
FIG. 1D represents the GLC profile for the reaction product of Example I, using a sulfuric acid catalyst and an alpha-methylstyrene diluent at 35° C. according to the conditions of United Kingdom Pat. No. 796,130 (crude reaction product)

FIG. 1D represents the GLC profile for the reaction product of Example I, using a sulfuric acid catalyst and an alpha-methylstyrene diluent at 35° C. according to the conditions of United Kingdom Pat. No. 796,130 (crude reaction product).

FIG. 1E represents the GLC profile for the reaction product of Example I, using a sulfuric acid catalyst, at 35° C. and an alpha-methylstyrene diluent according to the conditions of United Kingdom Pat. Spec. No. 796,130 (distilled reaction product).

Figure 2A:
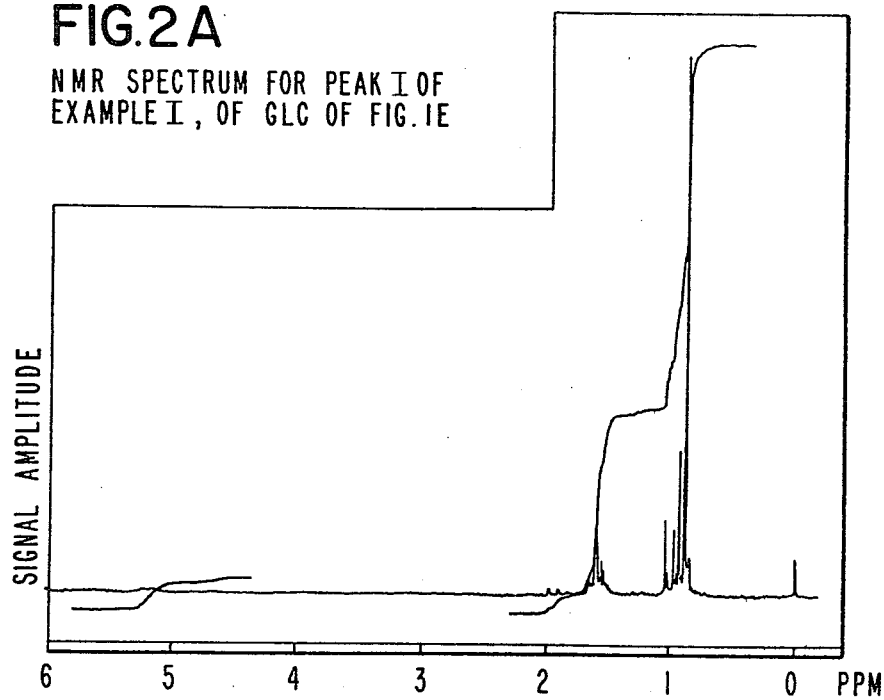
FIG. 2A represents the NMR spectrum for Peak 1 of the GLC profile of FIG. 1E.

FIG. 2A represents the NMR spectrum for Peak 1 of the GLC profile of FIG. 1E.

Figure 2B:
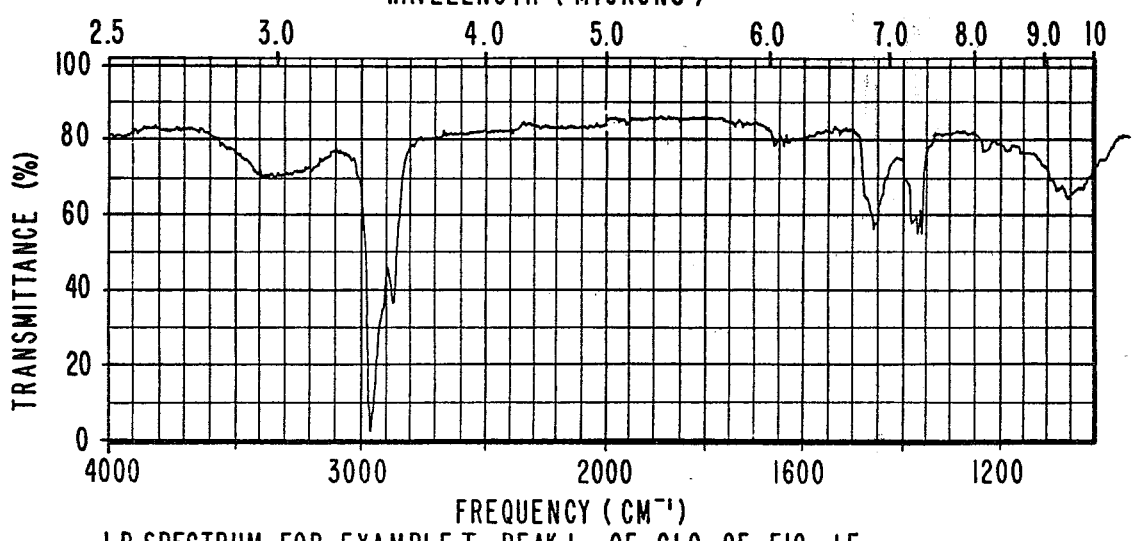
FIG. 2B represents the infra-red spectrum for Peak 1 of the GLC profile of FIG. 1E

FIG. 2B represents the infra-red spectrum for Peak 1 of the GLC profile of FIG. 1E FIG. 3A represents the NMR spectrum for Peak 2 of the GLC profile of FIG. 1E.

FIG. 3B represents the infra-red spectrum for Peak 2 of the GLC profile of FIG. 1E.

Figure 4:
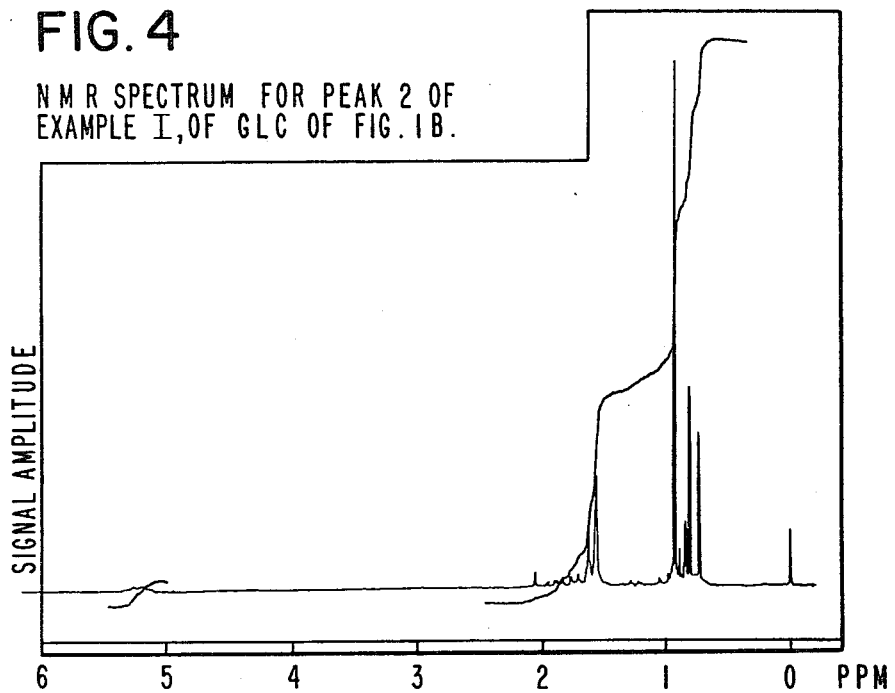
FIG. 4 represents the NMR spectrum for Peak 2 of the GLC profile of FIG. 1B.

FIG. 4 represents the NMR spectrum for Peak 2 of the GLC profile of FIG. 1B.

EXAMPLE II

Reaction:

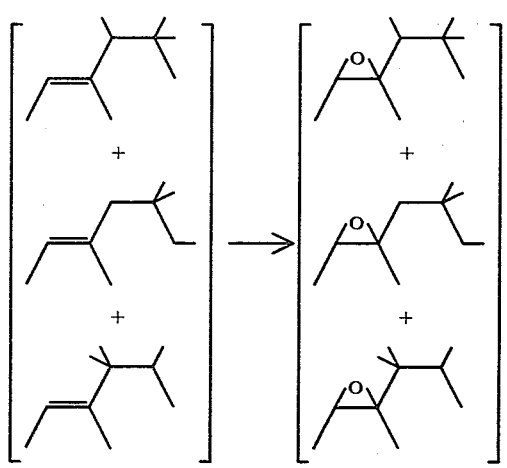

Into a 12 liter reaction flask, equipped with stirrer, reflux condenser, thermometer, addition funnel and cooling bath is placed 5,478 ml of di-isoamylene containing the compounds having the structures:

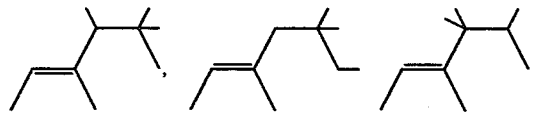

produced according to Example I. To the di-isoamylene material is added 120 grams of sodium carbonate. Over a period of 2.5 hours 5,130 grams (4,520 ml or 27 moles) of 40% peracetic acid is added to the reaction mass while maintaining the temperature at 20° C.–26° C. 200 grams additional sodium carbonate are then added to the reaction mass. The reaction mass is then cooled to room temperature and transferred to a 5 galon separatory funnel. The reaction mass is then washed as follows:
a. 1 liter water
b. Three 1.5 liter portions of 12.5% sodium hydroxide solution (to eliminate peroxides)
c. Three 1.5 liter portions of saturated sodium chloride solution The reaction mass is then distilled on an 18" Goodloe ® column, yielding the following fractions:

| Fraction No. | Vapor Temp. (°C.) | Liquid Temp. (°C.) | Pressure (mmHg) | Weight of Fraction (g) |
|---|---|---|---|---|
| 1 | 79/85 | 88/88 | 40/40 | 180 |
| 2 | 85 | 88 | 40 | 153 |
| 3 | 85 | 88 | 40 | 203 |
| 4 | 83/85 | 88/88 | 40 | 210 |
| 5 | 86 | 88 | 40 | 176 |
| 6 | 86 | 88 | 40 | 196 |
| 7 | 86 | 90 | 40 | 209 |
| 8 | 85/86 | 89/91 | 40 | 192 |
| 9 | 86 | 98 | 40 | 138 |
| 10 | 86 | 160 | 40 | 73 |
| 11 | 84 | 220 | 40 | 18 |

NMR, IR and mass spectral analysis yield the information that the reaction product contains three compounds having the structures:

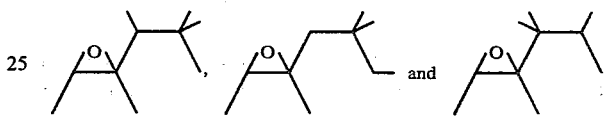

Figure 5:
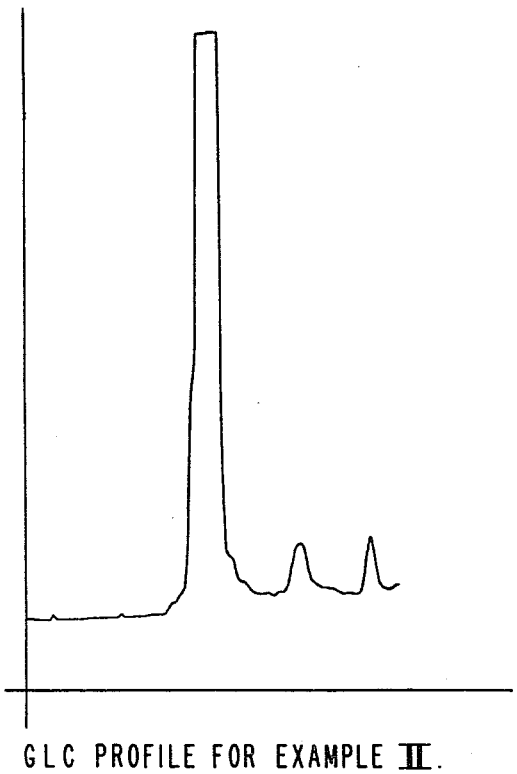
FIG. 5 is the GLC profile of the reaction product of Example II containing the compounds having the structures.

FIG. 5 is the GLC profile of the reaction product of Example II containing the compounds having the structures:

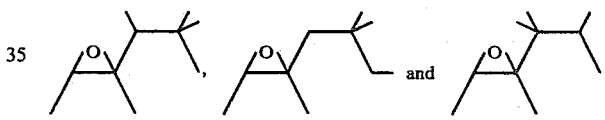

FIG. 6 is the NMR spectrum for the reaction product of Example II containing the compounds having the structures:

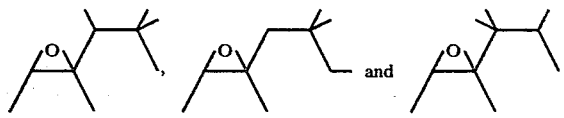

FIG. 7 is the infra-red spectrum for the reaction product of Example II containing the compounds having the structures:

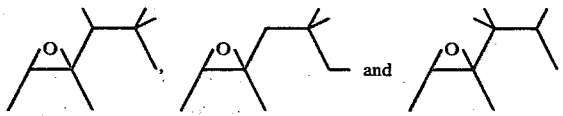

EXAMPLE III

The di-isoamylene epoxide product produced according to Example II has a woody, eucalyptol, minty note which may be utilized to a great extent in inexpensive functional products. The following pine fragrance demonstrates the use of this material in perfume compositions. In this case it is used in a concentration of 47.9%.

| | |
|---|---|
| Di-isoamylene epoxide of Example II | 479 |
| Isobornyl Acetate | 100 |
| Camphor | 10 |
| Terpineol | 25 |
| Fir Balsam Absolute (50% in Diethyl Phthalate | 20 |
| Coumarin | 4 |
| Linalool | 30 |
| Anethol | 2 |
| Fenchyl Alcohol | 10 |
| Lemon Terpenes Washed | 50 |
| Borneal | 5 |
| Galbanum Oil | 5 |
| Turpentine Russian | 150 |
| Pinus Pumilionus | 50 |
| Eucalyptol | 50 |
| 2,2,6-trimethyl-1-cyclohexene-1-carboxaldehyde | 5 |
| Maltol 1% in Diethyl Phthalate | 5 |

The presence of the di-isoamylene epoxide supports the pine notes and produces a considerable savings in the cost of the formulation. It also lends a pleasant and strong minty, herbaceous and woody character to this pine fragrance. The pine fragrance is extremely stable, particularly in hypochlorite bleaches as will be seen infra.

EXAMPLE IV

Preparation of a Cosmetic Powder Composition

A cosmetic powder is prepared by mixing in a ball mill, 100 grams of talcum powder with 0.25 grams of a perfume composition prepared according to Example III. It has an excellent piney aroma with woody, eucalyptol and minty nuances.

EXAMPLE V

Perfume Liquid Detergent

Concentrated liquid detergents (Lysine salt of n-dodecylbenzene sulfonic acid as more specifically described in U.S. Pat. No. 3,948,818, issued on Apr. 6, 1976) with eucalyptol-like, woody and minty aroma nuances are prepared containing 0.10%, 0.15%, 0.20%, 0.25%, 0.30% and 0.35% of the fragrance prepared according to Example III. They are prepared by adding and homogeneously mixing the appropriate quantity of fragrance formulation prepared according to Example III in the liquid detergent. The detergents all possess excellent piney aromas with woody, eucalyptol-like and minty undertones, the intensity increasing with greater concentrations of perfume composition of Example III.

EXAMPLE VI

Preparation of a Cologne and Handkerchief Perfume

The composition prepared according to Example III is incorporated into a cologne at concentrations of 2.0%, 2.5%, 3.0%, 3.5%, 4.0%, 4.5% and 5.0% in 75%, 80%, 85% and 90% aqueous food grade ethanol; and into a handkerchief perfume at concentrations of 15%, 20%, 25% and 30% (in 90% and 95% aqueous food grade ethanol). A distinctive and definite eucalyptol, woody, minty and piney aroma is imparted to the cologne and to the handkerchief perfume at all levels indicated above.

EXAMPLE VII

Preparation of Soap Composition

One hundred grams of soap chips (IVORY ®, produced by the Procter & Gamble Company, Cinncinati, Ohio) are mixed with one gram of the formulation of Example III until homogeneous compositions are obtained. In each of the cases, the homogeneous compositions are heated under three atmospheres pressure at 180° C. for a period of three hours and the resulting liquids are placed into soap molds. The resulting soap cakes, on cooling, manifest excellent eucalyptol-like, woody and minty aromas with an emphasis on the piney aspects of the aroma.

EXAMPLE VIII

Preparation of Solid Detergent Compositions

A detergent is prepared from the following ingredients according to Example I of Canadian Pat. No. 1,007,948:

| Ingredient | Percent by Weight |
|---|---|
| "Neodol ® 45-11 (a $C_{14}$–$C_{15}$ Alcohol ethoxylated with 11 moles of ethylene oxide | 12 |
| Sodium carbonate | 55 |
| Sodium citrate | 20 |
| Sodium sulfate, water brighteners | q.s. |

This detergent is a "phosphate-free" detergent. A total of 100 grams of said detergent is admixed with 0.10, 0.15, 0.20 and 0.25 grams of the pine perfume of Example III. The detergent sample has an excellent, woody, eucalyptol-like, minty and piney aroma.

EXAMPLE IX

Preparation of a Cosmetic Powder Composition

A cosmetic powder is prepared by admixing in a ball mill, 100 grams of talcum powder with 0.25 grams of one of the di-isoamylene epoxide compound mixture prepared according to Example II. The resulting cosmetic powder has an excellent eucalyptol-like, woody and minty aroma.

EXAMPLE X

Perfume Liquid Detergent

Concentrated liquid detergents (Lysine salt of n-dodecylbenzene sulfonic acid as more specifically described in U.S. Pat. No. 3,948,818, issued on Apr. 6, 1976) with eucalyptol-like, woody and minty aroma notes are prepared containing 0.10%, 0.15%, 0.20% and 0.25% of one or more of the di-isoamylene epoxides prepared according to Example II. They are prepared by adding and homogeneously mixing the appropriate quantity of di-isoamylene epoxide composition is liquid detergent. The detergents all possess eucalyptol-like, woody and minty aroma nuances, the intensity of each characteristic increasing with greater concentrations of di-isoamylene composition of Example II.

EXAMPLE XI

Preparation of Colognes and Handkerchief Perfumes

The di-isoamylene epoxide derivatives prepared according to Example II are incorporated into colognes at concentrations of 2.0%, 2.5%, 3.0%, 3.5%, 4.0% and 4.5% in 85% aqueous food grade ethanol; and into handkerchief perfumes at concentrations of 15%, 20%, 25% and 30% (in 80%, 85%, 90% and 95% aqueous ethanol solutions). Distinctive eucalyptol-like, woody and minty aroma nuances are imparted to the colognes and to the handkerchief perfumes at various levels indicated above.

EXAMPLE XII

Utilizing the procedure of Example I at column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:
1. A water "dissolvable" paper ("Dissolvo Paper").
2. Adogen 448 (m.p. about 140° F.) as the substrate coating; and
3. An outer coating having the following formulation (m.p. about 150° F.):
   57 percent $C_{20-22}$ HAPS
   22 percent isopropyl alcohol
   20 percent antistatic agent
   1 percent of one or more of the di-isoamylene epoxide derivatives of Example II.

Fabric-softening compositions eucalypol-like, woody and minty aroma characteristics essentially consist of a substrate having a weight of about 3 grams per 100 square inches; a substrate coating having a weight of about 1.85 grams per 100 square inches of substrate; and an outer coating having a weight of about 1.4 grams per 100 square inches of substrate, thereby providing a total aromatized substrate and outer coating weight ratio of about 1:1 by weight of the substrate. The woody, eucalyptol and minty aroma is imparted in a pleasant manner to the head space in the dryer on operation thereof, using the said dryer-added fabric softening nonwoven fabric.

In the following examples, Aromox ® DMC-W and Aromox ® DMMC-W are 30% aqueous solutions of dimethyl cocoamine oxide; and Aromox ® NCMDW is a 40% aqueous solution of N-cocomorpholine oxide produced by Armac Division of AKZO of Chicago, Ill.

EXAMPLE XIII

Four drops of one or a mixture of the di-isoamylene epoxide compositions prepared according to Example II is added to 2 grams of Aromox ® DMC-W to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody/eucalyptol-like/minty" aroma. Furthermore, no such characteristic "hypochlorite" aroma is retained on the hands of the individual handling such laundry in both the wet and the dry states.

EXAMPLE XIV

Aromox ® DMMC-W in various quantities is mixed with 0.1 gram of one or a mixture of the di-isoamylene epoxide compositions prepared according to Example II. The resulting premixes are then added to 200 grams of an aqueous 5% sodium hypochlorite solution. Sufficient 12.5 M aqueous NaOH is added to bring the pH of the mixture up to 13. The following results are obtained:

| Percentage Aromox DMMC-W | Clarity of hypochlorite solution after addition of premix |
|---|---|
| 0.23% | Clear after three days |
| 0.15% | Clear after three days |
| 0.08% | Initially slightly turbid; two phases exist after three days |

When the 5% aqueous sodium hypochlorite solutions are used as laundry bleaches, the resulting laundry batches on dry-out in an atmosphere of 65% relative humidity yields substantially no characteristic "hypochlorite" odor, but do have faint, pleasant "woody/eucalyptol/minty" aromas. Furthermore no such characteristic "hypochlorite" aroma is retained on the hands of the individual handling such laundry batches in both the wet and the dry states.

EXAMPLE XV

Two grams of Aromox ® DMMC-W are admixed with eight drops of one or a mixture of the di-isoamylene epoxide compositions prepared according to Example II. Each of the premix is then added with stirring to 200 grams of a 7% aqueous solution of lithium hypochlorite. Sufficient 3 M aqueous LiOH is added to bring the pH of the solution to 13.4. The mixtures are then heated to 120° F. and maintained at that temperature with stirring for a period of 1 week. The resulting solution remains clear in a single phase. When used as laundry bleaches, the resulting bleached laundry batches on dry-out in an atmosphere of 50% relative humidity retain a "woody, eucalyptol-like, minty" aroma; whereas without the use of the one or more di-isoamylene epoxides prepared according to Example II, the bleached laundry batches have faint characteristics disagreeable "hypochlorite" aroma.

EXAMPLE XVI

Two grams of Aromox ® DMMC-W are admixed with eight drops of one or a mixture of the di-isoamylene epoxide compositions produced according to Example II. The premixes are then added with stirring to 200 grams of a mixture containing 4.5% aqueous sodium hypochlorite and 4.5% aqueous lithium hypochlorite. Sufficient 4 M aqueous LiOH is added to bring the pH of the solutions to 13.4. The mixtures are then heated to 120° F. and maintained at that temperature for a period of one week. The resulting solutions remain clear in a single phase. When used as laundry bleaches, the resulting bleached laundry batches on dry-out in an atmosphere of 50% relative humidity retain a "woody, eucalyptol-like and minty" aroma; whereas without the use of the di-isoamylene epoxide(s) prepared according to Example II, the bleached laundry batches have faint characteristic disagreeable "hypochlorite" aroma.

EXAMPLE XVII

Two grams of Aromox ® DMMC-W are admixed with eight drops of one or a mixture of di-isoamylene epoxide products produced according to Example II. These premixes are then added with stirring to 200 grams of mixture containing 4% aqueous sodium hypochlorite and 4% aqueous lithium hypochlorite. Sufficient 2 M aqueous NaOH is added to bring the pH of the solutions to 13.4. The mixtures are then heated to 110° F. and maintained at that temperature with stirring for a period of 2 weeks. The resulting solutions remain clear as a single phase when used as laundry bleaches. The resulting bleached laundry batches on dry-out in an atmosphere of 50% relative humidity retain a "wood, eucalyptol-like, minty" aroma; whereas without the use of the di-isoamylene epoxide compositions of Example II the bleached laundry batches have faint characteristic disagreeable "hypochlorite" aroma.

EXAMPLE XVIII

Four drops of one or a mixture di-isoamylene epoxide products produced according to Example II are added to 1.5 grams of Aromox ® NCMDW to produce a clear premix. The clear premix is added to 200 grams of CLOROX ® with stirring resulting in a clear stable single phase solution. Sufficient 1 M aqueous NaOH is added to bring to pH to the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, eucalyptol-like, minty" aroma. Furthermore, no such characteristic "hypochlorite" aroma is retained on the hands of the individual handling such laundry in both the wet and the dry states.

EXAMPLE XIX

Four drops of one or a mixture of the di-isoamylene epoxide product produced according to Example II, is added to 1 gram of n-undecyl dimethyl amine oxide to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach the resulting laundry on dry-out in an atmosphere of 65% relative humidity yields substantially no characteristic "hypochlorite" odor but does have a faint pleasant "woody, eucalyptol-like, minty" aroma. Furthermore, no such characteristic "hypochlorite" aroma is retained on the hands of the individual handling such laundry in both the wet and the dry states.

EXAMPLE XX

Four drops of one or a mixture of the di-isoamylene epoxide products produced according to Example II is added to 1 gram of n-dodecyl dimethyl amine oxide to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, eucalyptol-like, minty" aroma. Furthermore, no such characteristic "hypochlorite" aroma is retained on the hands of the individual handling such laundry in both the wet and the dry states.

EXAMPLE XXI

One gram of n-tridecyl dimethyl amine oxide is admixed with eight drops of one or a mixture of the di-isoamylene epoxide compositions of Example II. This premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a "woody, eucalyptol-like, minty" aroma; whereas without the use one or the mixture of the di-isoamylene eposide compositions of Example II the bleach laundry has a faint characteristic disagreeable "hypochlorite" aroma.

What is claimed is:

1. A process for augmenting or enhancing the aroma of a solid or liquid anionic, cationic, nonionic or zwitterionic detergent comprising the step of adding to a solid or liquid anionic, cationic, nonionic or zwitterionic detergent base an aroma augmenting or enhancing quantity of at least one epoxide compound defined according to the structure:

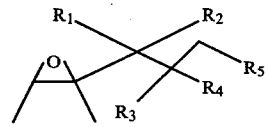

wherein $R_1$, $R_2$, $R_3$, $R_4$ and $R_5$ are the same or different and each represents hydrogen or methyl with the proviso that (i) the sum total of carbon atoms in $R_1$, $R_2$, $R_3$, $R_4$ and $R_5$ is three, and (ii) $R_1$ and $R_2$ represent hydrogen when $R_5$ represents methyl, and (iii) when either $R_1$ or $R_2$ is methyl, $R_5$ is hydrogen.

2. A process for augmenting or enhancing the aroma of a solid or liquid anionic, cationic, nonionic or zwitterionic detergent comprising the step of adding to a solid or liquid anionic, nonionic, cationic or zwitterionic detergent base an aroma augmenting or enhancing quantity of a composition comprising epoxide compounds produced according to the process comprising the steps of reacting isoamylene having the structure:

with a Lewis acid or a mineral acid to form a mixture of diisoamylenes having the structures:

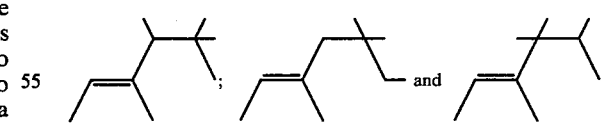

and then reacting the said mixture of diisoamylenes with a peracid in order to form a mixture of epoxides having the structures:

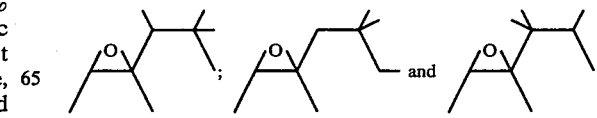

* * * * *